(12) United States Patent
Yanagawa et al.

(10) Patent No.: US 8,017,724 B2
(45) Date of Patent: Sep. 13, 2011

(54) METHOD FOR PRODUCING SULFONIC ACID GROUP-CONTAINING CARBONACEOUS MATERIAL, SOLID ACID CATALYST, METHOD FOR PRODUCING ALKYLATION REACTION PRODUCT, AND METHOD FOR PRODUCING OLEFIN POLYMER

(75) Inventors: Shinichirou Yanagawa, Yokohama (JP); Hidesato Kondo, Yokohama (JP); Michikazu Hara, Yokohama (JP)

(73) Assignees: Nippon Oil Corporation, Tokyo (JP); Tokyo Institute of Technology, Tokyo (JP)

( * ) Notice: Subject to any disclaimer, the term of this patent is extended or adjusted under 35 U.S.C. 154(b) by 0 days.

(21) Appl. No.: 12/599,389

(22) PCT Filed: May 8, 2008

(86) PCT No.: PCT/JP2008/058558
§ 371 (c)(1),
(2), (4) Date: Mar. 18, 2010

(87) PCT Pub. No.: WO2008/143008
PCT Pub. Date: Nov. 27, 2008

(65) Prior Publication Data
US 2010/0216953 A1    Aug. 26, 2010

(30) Foreign Application Priority Data

May 11, 2007 (JP) ................................. 2007-126882

(51) Int. Cl.
*C08F 6/00* (2006.01)
*C08G 64/00* (2006.01)

(52) U.S. Cl. .................. 528/481; 525/505; 526/346

(58) Field of Classification Search ............... 525/505; 526/346; 528/481
See application file for complete search history.

(56) References Cited

U.S. PATENT DOCUMENTS

| | | |
|---|---|---|
| 4,265,768 A | 5/1981 | Beasley et al. |
| 2008/0227996 A1 | 9/2008 | Hara et al. |

FOREIGN PATENT DOCUMENTS

| | | |
|---|---|---|
| EP | 0031586 | 7/1981 |
| JP | 2004-238311 | 8/2004 |
| JP | 2007-039313 | 2/2007 |
| JP | 2007-172887 | 7/2007 |
| WO | 2005/029508 | 3/2005 |
| WO | 2006/126721 | 11/2006 |

OTHER PUBLICATIONS

Takagaki et al., "Synthesis condition and catalysis of carbon-based solid acid catalysts", 85th Annual Meeting (Spring) of the Chemical Society of Japan (2005), 2B5-43, along with an English language translation, 2005.
Hara et al., Nature, vol. 438, p. 178, Nov. 10, 2005.
Hara et al., "Synthesis and characterization of carbon-based solid strong acid having large surface area,"96th Meeting of the Catalysis Society of Japan (2005), 4E-21, along with an English language translation, 2005.
Baker et al., "Sulfur-functionalized carbon aerogels: a new approach for loading high-surface-area electrode nanoarchitectures with precious metal catalysts", Journal of Non-Crystalline Solids, vol. 350, pp. 80-87, 2004.
Hara et al., Petcotech, vol., 29, No. 6, pp. 411-416, along with an English language translation, 2006.
International Search Report dated Aug. 5, 2008 that issued with respect to PCT/JP2008/058558.
Masakazu Toda et al., "Biodiesel Made With Sugar Catalyst", Nature, vol. 438, XP002635581, Nov. 10, 2005, pp. 178.
Henry Preiss et al., "Preparation of Carbon Catlysts by Hydrothermal Treatment of a Carbonaceous Hydrogel", Carbon, vol. 32, No. 4, XP002635582, Dec. 31, 1994, pp. 587-592.
Emily J. Zanto et al., "Sol-Gel Derived Carbon Aerogels and Xerogels: Design of Experiments Approach to Material Synthesis", Ind. Eng. Chem. Res., vol. 41, XP002635583, Dec. 31, 2002, pp. 3151-3162.
Search report from E.P.O. that issued with respect to patent family member European Patent Application No. 08752449.2, mail date is May 20, 2011.

*Primary Examiner* — Terressa Boykin
(74) *Attorney, Agent, or Firm* — Greenblum & Bernstein, P.L.C.

(57) ABSTRACT

The method for producing a sulfonic acid group-containing carbonaceous material of the present invention comprises the step of carbonizing and sulfonating a polymer having a structural unit derived from resorcinol by heating in an inert gas atmosphere to obtain a sulfonic acid group-containing carbonaceous material. A catalyst comprising the resulting sulfonic acid group-containing carbonaceous material is useful for producing a target substance with high efficiency in various reactions in hydrophobic media such as alkylation reaction and polymerization reaction of olefins.

13 Claims, No Drawings

METHOD FOR PRODUCING SULFONIC ACID GROUP-CONTAINING CARBONACEOUS MATERIAL, SOLID ACID CATALYST, METHOD FOR PRODUCING ALKYLATION REACTION PRODUCT, AND METHOD FOR PRODUCING OLEFIN POLYMER

TECHNICAL FIELD

The present invention relates to a method for producing a sulfonic acid group-containing carbonaceous material, a solid acid catalyst, a method for producing an alkylation reaction product, and a method for producing an olefin polymer.

BACKGROUND ART

Sulfuric acid is an important catalyst widely used in various chemical reactions. However, sulfuric acid has a large number of problems. For example, sulfuric acid is generally required in large amounts, causes apparatus corrosion, and requires the steps of separating, collecting, purifying and reusing sulfuric acid from the product after the reaction, the steps of neutralizing, the sulfuric acid remaining in the product, removing and discarding the salt generated thereby, and treating the wastewater treatment, and the like, and further, these steps require a lot of energy. In addition, while hydrogen fluoride is known as a liquid acid catalyst with comparatively fewer waste problems, problems thereof are that hydrogen fluoride is so corrosive that a special alloy is required for a reaction apparatus, and that hydrogen fluoride is easily volatilized.

Therefore, use of a solid acid catalyst as a substitute for a mineral acid catalyst such as sulfuric acid has been considered. A solid acid catalyst is useful as a catalyst for various chemical reactions because the above various steps after the reactions can be omitted or substantially simplified without apparatus corrosion, and various solid acids have been developed. Typical solid acids are inorganic compounds such as silica-alumina, crystalline aluminosilicate (synthetic zeolite), solid phosphoric acid and heteropoly acid.

For example, alkylation reactions such as for production of various alkyl aromatics and aralkyl compounds, and in addition, production of isoparaffin useful for production of high-octane gasoline are industrially very important reaction procedures, and an acid catalyst is used for the reactions. The above-described liquid strong acid such as sulfuric acid or hydrogen fluoride has been conventionally used. However, due to the above-described problems; the solid acid catalyst has recently been used.

In addition, polymerization reactions of olefins are important, for example, as methods for producing various polymers such as polystyrene and polybutene, and a solid acid catalyst is used also for the reactions.

However, the solid acid catalyst used for the conventional alkylation reaction or polymerization reaction of olefins has various problems. For example, examples of the solid acid catalyst used for alkylation reaction include synthetic zeolite catalysts and solid phosphoric acid catalysts. However, the synthetic zeolite catalysts are expensive. Also, the solid phosphoric acid catalysts are complicated in use, for example because the elution of phosphoric acid that is an active ingredient from the catalyst cannot be avoided, so a phosphoric acid component needs to be replenished as necessary. In addition, a strong acid ion-exchange resin, a polymer having a sulfonic acid group on the skeleton of a cross-linked polystyrene, is also known, but its range of use is limited due to problems such as the low heat resistance and expensiveness of the resin. The fluorine-substituted olefin polymer-based, very strong solid acid "NAFION" (a registered trademark of DuPont) having heat resistance and the like have been also developed, but they are too expensive to be used for industrial purposes.

On the other hand, Lewis acid-type catalysts such as aluminum chloride and boron trifluoride are generally used for the polymerization reaction of olefins. However, problems thereof include that these acid catalysts are highly corrosive to metal materials, and the acid catalyst is eluted into a reaction product, so a neutralization treatment of the reaction product is required.

Under these background, a sulfonic acid group-containing carbonaceous material obtained by carbonizing and sulfonating an organic substance such as an aromatic compound, petroleum heavy oil or sugars by heating has been developed. The sulfonic acid group-containing carbonaceous material has recently been attracting attention due to its high activities for various chemical reactions as a solid acid catalyst, excellent heat resistance, inexpensiveness and the like, and the evaluations thereof as a catalyst for esterification reaction of a fatty acid, hydrolysis reaction of an ester, alkylation reaction, hydration reaction of an olefin, and the like are being tried (Patent Document 1, Patent Document 2, Non-Patent Document 1, Non-Patent Document 2, and Non-Patent Document 3).

In addition, for example, in an alkylation reaction, in order to increase the activity as an acid catalyst, a method of heat-treating a composition of an organic substance and phosphoric acid to carbonize the organic substance and thereafter extracting the phosphoric acid is known (Non-Patent Document 4).

Furthermore, a catalyst obtained by further supporting on a support a solid acid catalyst obtained by carbonizing and sulfonating an organic substance is known (Non-Patent Document 3).

Patent Document 1: Japanese Patent Laid-Open No. 2004-238311
Patent Document 2: International Patent Publication No. WO 2005/029508 A1
Non-Patent Document 1: Domen et al., "Synthesis conditions and catalysis of carbon-based strong solid acids," 85th Annual Meeting (Spring) of the Chemical Society of Japan (2005), 2B5-43
Non-Patent Document 2: Hara, M. et al. Nature, 438(10), 178, November (2005)
Non-Patent Document 3: Nara et al., PETROTECH, 29(6), 411 (2006)
Non-Patent Document 4: Ham et al., "Synthesis and characterization of carbon-based solid strong acid having large surface area," 96th Meeting of the Catalysis Society of Japan (2005), 4E-21

DISCLOSURE OF THE INVENTION

However, even the above-described conventional solid acid catalyst still has room for improvement as one that can be produced by a practical method and has a high catalytic activity for various chemical reactions including reactions in hydrophobic media such as alkylation reaction and polymerization reaction of olefins.

Specifically, in the method disclosed in Non-Patent Document 4 described above, it is required that an organic substance and a corrosive phosphoric acid as starting materials be mixed in a good dispersion state, and further that the phosphoric acid be removed by extraction after carbonization, so the catalyst production process is complicated, and treatment of waste phosphoric acid is also required.

In addition, the method disclosed in Non-Patent Document 3 described above requires complicated operations such as preliminarily impregnating a support with an organic substance to support the substance on the support and thereafter carbonizing and sulfonating the organic substance. Furthermore, an application of the solid acid catalyst obtained by the method to polymerization of olefins is not mentioned at all.

The present invention has been made in view of the above conditions, and an object of the present invention is to provide a method for producing a sulfonic acid group-containing carbonaceous material having high reaction activities as a solid acid catalyst useful for various reactions in various hydrophobic media, such as alkylation reaction and polymerization reaction of olefins. In addition, other objects of the present invention are to provide a solid acid catalyst using the sulfonic acid group-containing carbonaceous material and a method for producing an alkylation reaction product and a method for producing olefin polymers using the solid acid catalyst.

As a result of intensive studies to achieve the above objects, the present inventors have found that a polymer having a structural unit derived from resorcinol is carbonized and sulfonated by heating, whereby a sulfonic acid group-containing carbonaceous material having high activities as a solid acid catalyst for various chemical reactions in hydrophobic media is obtained. The present invention has been accomplished thereby.

More specifically, the present invention provides a method for producing a sulfonic acid group-containing carbonaceous material comprising a first step of carbonizing and sulfonating a polymer having a structural unit derived from resorcinol by heating in an inert gas atmosphere to obtain a sulfonic acid group-containing carbonaceous material.

In the present invention, the above polymer is preferably obtained by addition condensation of resorcinol or a mixture comprising resorcinol and an aromatic hydroxy compound other than resorcinol with aldehydes in the presence of an acid catalyst or a basic catalyst; and is more preferably obtained by addition condensation of resorcinol or a mixture comprising 50% by weight or more of resorcinol and 50% by weight or less of phenol with formaldehyde in the presence of a basic catalyst.

In addition, the above basic catalyst is preferably a sodium carbonate catalyst.

Furthermore, as the above polymer, one obtained by removing water and/or solvent from a gel comprising a reaction product by addition condensation reaction of resorcinol or a mixture comprising resorcinol and an aromatic hydroxy compound other than resorcinol with aldehydes in the presence of a basic catalyst and the water and/or solvent can be preferably used.

In addition, the above first step preferably comprises a second step of performing carbonization of the above polymer in an inert gas atmosphere at a temperature of from 300 to 600° C. for 1 to 100 hours and a third step of performing sulfonation of a treated product obtained in the second step by concentrated sulfuric acid.

The sulfonic acid group content of the sulfonic acid group-containing carbonaceous material obtained in the first step is preferably 0.3 mmol/g or more.

In addition, the present invention provides a solid acid catalyst comprising the sulfonic acid group-containing carbonaceous material obtained by the method for producing a sulfonic acid group-containing carbonaceous material of the present invention.

Furthermore, the present invention provides a method for producing an alkylation reaction product comprising performing an alkylation reaction of a prescribed reaction substrate in the presence of the solid acid catalyst of the present invention.

In the method for producing an alkylation reaction product of the present invention, the above reaction substrate is not particularly limited, and it is particularly preferable when the reaction substrate is an aromatic compound.

Also, it is preferable as well when the reaction substrate is a paraffinic hydrocarbon having a tertiary carbon atom.

In addition, the present invention provides a method for producing an olefin polymer comprising performing a polymerization reaction of olefins in the presence of the solid acid catalyst of the present invention.

EFFECT OF THE INVENTION

The method for producing a sulfonic acid group-containing carbonaceous material of the present invention can easily and inexpensively produce a sulfonic acid group-containing carbonaceous material having high reaction activities as a solid acid catalyst useful for various reactions in various hydrophobic media, such as alkylation reaction and polymerization reaction of olefins, and is very useful as a production method that can supply a sulfonic acid group-containing carbonaceous material in large amounts for industrial use.

In addition, the solid acid catalyst of the present invention comprises a sulfonic acid group-containing carbonaceous material obtained by the method for producing a sulfonic acid group-containing carbonaceous material of the present invention, thereby having an excellent activity as a solid acid catalyst. Furthermore, the solid acid catalyst of the present invention do not require the steps of neutralizing and purifying the catalyst after the reactions and the like, is easily separated to be reusable and is also excellent in suppression of apparatus corrosion. Therefore, the solid acid catalyst of the present invention is very useful in that, for example, in reactions such as alkylation reaction and polymerization reaction of olefins, the target substance can be inexpensively and effectively produced.

Furthermore, according to the method for producing an alkylation reaction product and method for producing olefin polymer of the present invention, the above solid acid catalyst of the present invention is used in the respective method, whereby the target substance can be inexpensively and effectively produced.

BEST MODES FOR CARRYING OUT THE INVENTION

The preferred embodiments of the present invention will be described in detail hereinbelow.
(Method for Producing Sulfonic Acid Group-Containing Carbonaceous Material)

The method for producing a sulfonic acid group-containing carbonaceous material of the present invention comprises a step of carbonizing and sulfonating a polymer having a structural unit derived from resorcinol by heating in an inert gas atmosphere to obtain a sulfonic acid group-containing carbonaceous material (first step).

In the present invention, "a polymer having a structural unit derived from resorcinol" comprises a polymer obtained by addition condensation reaction of resorcinol with aldehydes using an acid catalyst or a basic catalyst (a polymer without having a structural unit derived from an aromatic hydroxy compound other than resorcinol; hereinafter, referred to as "polymer (A)") and a polymer obtained by addition condensation reaction of a mixture comprising resorcinol and an aromatic hydroxy compound other than resorcinol with an aldehyde using an acid catalyst or a basic catalyst (hereinafter, referred to as "polymer (B)") and a modified resin of polymer (A) or (B).

The aldehyde used as a raw material of the polymer (A) includes formaldehyde, acetaldehyde, furfural and the like. In particular, formaldehyde is preferred. In addition, the acid catalyst includes hydrochloric acid, oxalic acid and the like. Furthermore, the basic catalyst includes sodium carbonate, potassium carbonate, lithium carbonate, sodium hydroxide, potassium hydroxide, lithium hydroxide, barium carbonate, sodium phosphate, lithium phosphate, potassium phosphate, and the like. In particular, sodium carbonate is preferred.

Preferred example of the polymer (A) includes resorcinol-formaldehyde resin obtained by addition condensation of resorcinol with formaldehyde, for details, a novolac type resorcinol resin obtained by addition condensation of resorcinol with formaldehyde using an acid catalyst and a resol type resorcinol resin obtained by addition condensation of resorcinol with formaldehyde using a basic catalyst.

Also, as the polymer (A), one obtained by removing a solvent from a gel comprising a reaction product by addition condensation reaction of resorcinol with an aldehyde and a basic catalyst and the solvent can be preferably used. In particular, resorcinol resin obtained by drying RF wet gel in a vacuum obtained by addition condensation of resorcinol with formaldehyde using a basic catalyst is called RF xerogel and is particularly preferably used. In addition, RF cryogel obtained by lyophilizing RF wet gel is preferably used.

In addition, as an aromatic hydroxy compound other than resorcinol used as a raw material of the polymer (B), a compound obtained by substituting hydrogen of an aromatic ring with hydroxy group, such as phenol or naphthalenediol, is preferable, and phenol is particularly preferable. Upon producing the polymer (B), in a mixture of resorcinol and an aromatic hydroxy compound other than resorcinol, it is preferable that the content of resorcinol is 50% by weight or more and the content of the aromatic hydroxy compound other than resorcinol is 50% by weight or less. When the content of the aromatic hydroxy compound other than resorcinol exceeds 50% by weight, reactivity of condensation reaction is lowered, so the target polymer is likely to be difficult to obtain.

Also, as the aldehydes used as a raw material of the polymer (B), formaldehyde, acetaldehyde, furfural and the like are used. In particular, as well as the case where resorcinol is singularly subjected to addition condensation, a resin obtained by addition condensation with formaldehyde is preferable. For details, a novolac type resin obtained by addition condensation of a mixture comprising resorcinol and an aromatic hydroxy compound other than resorcinol with an aldehyde using an acid catalyst (hereinafter, referred to as "MRF novolac resin") and a resol type resin obtained by addition condensation of a mixture comprising resorcinol and an aromatic hydroxy compound other than resorcinol with an aldehyde using a basic catalyst (hereinafter, referred to as "MRF resol resin") are preferable. A xerogel obtained by drying a wet gel in a vacuum obtained by polymerizing using a basic catalyst (hereinafter, referred to as "MRF wet gel") (hereinafter, referred to as "MRF xerogel") is particularly preferably used. A cryogel obtained by lyophilizing MRF wet gel (called MRF cryogel) is also preferably used.

The basic catalyst used in the production of MRF wet gel includes, as well as the case where resorcinol is singularly used, sodium carbonate, potassium carbonate, lithium carbonate, sodium hydroxide, potassium hydroxide, lithium hydroxide, barium carbonate, sodium phosphate, lithium phosphate, potassium phosphate and the like, and sodium carbonate is particularly preferable.

In the method for producing a sulfonic acid group-containing carbonaceous material of the present invention, the above polymers are subjected to carbonization and sulfonation in an inert gas atmosphere. The carbonization and sulfonation may be simultaneously performed, or the sulfonation may be performed after the carbonization, and a method of performing the sulfonation after the carbonization is preferable. Particularly, when the above-described RF xerogel or RF cryogel, or MRF xerogel or MRF cryogel is used as a raw material, the method of performing the sulfonation after the carbonization is preferable. Preferred aspects in the case where the sulfonation is performed after the carbonization will be described hereinbelow.

The conditions for the carbonization are properly selected depending on the type of raw materials to be used, properties of the intended sulfonic acid group-containing carbonaceous material, and the like. The carbonization is preferably performed by heating in an inert gas atmosphere such as nitrogen or argon, whereby an amorphous black solid (carbonized materials) is obtained. The carbonization temperature is from 300 to 600° C., preferably from 350 to 550° C., and further preferably from 370 to 550° C. When the temperature of carbonization is below the lower limit of the above range, a sulfonic acid group-containing carbonaceous material obtained by the sulfonation is likely to have problems such as having small specific surface area, poor heat resistance, or much content of soluble materials in water or organic substance. On the other hand, when the carbonization temperature is above the upper limit of the above range, a sufficient amount of sulfonic acid groups cannot be provided upon the sulfonation, and the catalytic activities for various chemical reactions of the resulting sulfonic acid group-containing carbonaceous are likely to be insufficient. The heating time in the carbonization is from 1 to 100 hours, and preferably from 2 to 15 hours. When the time of carbonization is below the lower limit of the above range, a sulfonic acid group-containing carbonaceous material obtained by the sulfonation is likely to cause problems such as having poor heat resistance, or much content of soluble materials in water, organic substance, or the like. On the other hand, when the heating time is within the above range, the necessary carbonization progresses sufficiently, so it is unnecessary to spend a time above the upper limit. Incidentally, a substance obtained by carbonizing the above RF cryogel or MRF cryogel and a substance obtained by carbonizing the above RF xerogel or MRF xerogel are called carbon cryogel and carbon xerogel, respectively.

The conditions for the sulfonation are properly selected depending on the type of raw materials to be used and properties of the intended sulfonic acid group-containing carbonaceous material. The sulfonation is performed by heating a carbonized material obtained by the carbonization in concentrated sulfuric acid or fuming sulfuric acid, whereby a sulfonic acid group is added to the skeleton of the carbonized material. The amount of concentrated sulfuric acid or fuming sulfuric acid to be used is not particularly limited and is 5 to 100 times (mass ratio) and preferably 10 to 80 times as the amount of carbonized material to be sulfonated. When the amount is below the lower limit of the above range, a sufficient amount of sulfonic acid groups cannot be provided to the carbonized material, and the catalytic activities for various chemical reactions of the resulting sulfonic acid group-containing carbonaceous material are likely to be insufficient. On the other hand, when the amount is above the upper limit of the above range, excessive concentrated sulfuric acid or fuming sulfuric acid is used, so the cost is increased including the disposal of used sulfuric acid. The temperature of sulfonation is from 100 to 450° C. and preferably from 100 to 200° C. When the temperature of sulfonation is below the lower limit of the above range, a sufficient amount of sulfonic acid groups is difficult to be provided to the carbonized material, and the catalytic activities for various chemical reactions of the resulting sulfonic acid group-containing carbonaceous material are likely to be lowered. On the other hand, when the temperature of sulfonation is above the upper limit of the above range, the added sulfonic acid groups are likely to decompose. The time of sulfonation is preferably from 0.5 to 30 hours. When the time of sulfonation is below the lower limit of the above range, a sufficient amount of sulfonic groups cannot be provided to the carbonized material, and the catalytic activities for various chemical reactions of the resulting sulfonic acid group-containing carbonaceous material are likely to be insufficient. On the other hand, necessary sulfonation sufficiently progresses at the upper limit time of the above range, so it is unnecessary to spend a time above the upper limit time.

For a treated product after the carbonization and sulfonation steps, excessive sulfuric acid is removed by washing the sulfonated product preferably with hot water, and the resulting product was further dried, whereby the intended sulfonic acid group-containing carbonaceous material can be obtained. The sulfonic acid group-containing carbonaceous material obtained in the present invention is normally black powder. The washing with hot water can be easily carried out, for example, under reflux at about 100° C. by means of Soxhlet extraction or the like. Also, the washing time can be shortened by washing at higher temperature under pressure.

The sulfonic acid group content of the sulfonic acid group-containing carbonaceous material obtained by the production method of the present invention is 0.3 mmol/g or more and preferably 0.5 mmol/g or more. When the sulfonic acid group content is below the lower limit of the above range, the activities as a solid acid catalyst for various chemical reactions of the sulfonic acid group-containing carbonaceous material are likely to be insufficient. There is no particular restriction on the upper limit of the sulfonic acid group content. In the present invention, the sulfonic acid group content was calculated by determination of ion exchange capacity using a sodium chloride solution. More specifically, a prescribed amount of pulverized sulfonic acid group-containing carbonaceous material molded body was added to a sodium chloride solution, and the mixture was stirred for certain period of time to exchange a proton of the sulfonic acid group for a sodium ion. The amount of HCl produced by ion exchange was quantitatively determined by neutralizing titration, to calculate the sulfonic acid group content. Incidentally, an exchange reaction between a proton of the sulfonic acid group and a sodium ion is as the following equation (1).

R—SO$_3$H+NaCl→R—SO$_3$Na+HCl    (1)

[In the equation (1), R represents a carbon residue of the sulfonic acid group-containing carbonaceous material.]

In general, the degree of carbonization upon carbonizing an organic substance by heating is frequently represented by the degree of graphitization, and the intensity ratio of G-peak which appears near a wavenumber of 1580 cm$^{-1}$ and D-peak which appears near 1400 cm$^{-1}$ in Raman spectroscopy is utilized as one of the indexes showing the degree of graphitization. For example, in the conventional sulfonic acid group-containing carbonaceous material using aromatic hydrocarbon, heavy oil, glucose and the like as starting materials, disclosed in Non-Patent Document 5, the degree of graphitization is determined according to Raman spectroscopy, or the size of carbon sheet is estimated using the degree of graphitization. However, with respect to the sulfonic acid group-containing carbonaceous material obtained by the production method of the present invention, a clear Raman spectrum is not obtained, and the degree of carbonization cannot be confirmed based on this index. This difference supports that the sulfonic acid group-containing carbonaceous material obtained by the production method of the present invention is different from the conventional sulfonic acid group-containing carbonaceous material in its structure.

In addition, in case of the sulfonic acid group-containing carbonaceous material obtained by the production method of the present invention, any structure cannot be confirmed from an X-ray diffraction pattern, so the material is substantially amorphous.

Also, activated carbon obtained by carbonizing an organic substance at high temperature has a specific surface area of from 1000 to 3000 m$^2$/g (see, for example, Encyclopaedia Chimica, published by KYORITSU SHUPPAN CO., LTD). However, even if activated carbon is sulfonated, a sulfonic acid group is hardly added, and an activity as a solid acid catalyst is hardly exhibited. In this regard, activated carbon differs from the sulfonic acid group-containing carbonaceous material obtained by the production method of the present invention.

(Solid Acid Catalyst)

As described above, the sulfonic acid group-containing carbonaceous material obtained by the production method of the present invention differs from the conventionally known sulfonic acid group-containing carbonaceous material or activated carbon and exhibits excellent properties in the case of being used as a solid acid catalyst. More specifically, the sulfonic acid group-containing carbonaceous material obtained by the production method of the present invention has an acid intensity and acid amount to an extent to be useful for various chemical reactions as a solid acid catalyst. Moreover, the solid acid catalyst of the present invention comprising the sulfonic acid group-containing carbonaceous material exhibits excellent functions under hydrophobic conditions such as alkylation reaction and polymerization reaction of olefins particularly as an acid catalyst.

The solid acid catalyst of the present invention may be a powder shape and also may be formed into a granular, spherical, plate, or pellet shape. When the solid acid catalyst of the present invention is formed into these shapes, an inorganic substance called binder may be blended to carry out forming. The binder is blended for the purpose of the improvement of formability, the improvements of mechanical properties such as strength of formed catalyst, rub resistance and the like, and alumina, alumina-boria, silica-alumina and the like are preferably used.

(Method for Producing Alkylation Reaction Product)

In the method for producing an alkylation reaction product of the present invention, an alkylation reaction of a prescribed reaction substrate is performed in the presence of the solid acid catalyst of the present invention.

The reaction substrate that is a raw material to be alkylated is not particularly limited, and various aromatic compounds or the like are used. Benzene, toluene, xylene and the like are the typical ones. Polyaromatic compounds such as naphthalene and anthracene can be also used. Various alkyl aromatics of which aromatic ring is substituted by an alkyl group can be also preferably used. In addition, those of which aromatic ring is substituted by a polar group, for example, alkoxy substitution products such as anisole, acyl substitution products like acetophenone and benzophenone are also preferably used. Halogen-substituted aromatics are also used. Also, as a reaction substrate in the alkylation reaction, paraffins having a tertiary carbon such as isobutane and isopentane are also preferably used.

An alkylating agent is not particularly limited, and various olefins and halogenated hydrocarbons and the like are used. Styrene and isobutylene or halogenated benzyls and alkyl halides and the like are the typical ones. Alcohols such as benzyl alcohol are also preferably used. While isooctane obtained by alkylating isobutane with isobutene or normal butene is important as a gasoline base with a high octane number as described above, the sulfonic acid group-containing carbonaceous material obtained by the method of the present invention and the solid acid catalyst of the present invention can be also preferably used for the above reaction. As the reaction conditions in the alkylation reaction, the reaction conditions suitable for various raw materials can be adopted. However, when the reaction temperature exceeds 250° C., it is not preferred since the sulfonic acid group-containing carbonaceous material may decompose and a sulfonic acid group may be eliminated. The reaction pressure and reaction time are not particularly limited, and the same conditions as the normal solid acid catalyst can be adopted.

Also, the type of reactor to perform the alkylation reaction is not particularly limited, and any one of batch, continuous and semicontinuous types may be used. Also, any form of reactor, such as tank reactor, column reactor and loop reactor, may be used. The form of contacting the catalyst with the reactant may be any one of suspension phase, fixed bed and the like. In particular, the form that suspends the catalyst in a tank reactor equipped with a stirring apparatus or the form that continuously let flow the reactant through the catalyst in a fixed bed is preferably adapted.

(Method for Producing Olefin Polymer)

In the method for producing an olefin polymer of the present invention, a polymerization reaction of olefins is performed in the presence of the solid acid catalyst of the present invention.

Olefin subjected to the polymerization reaction is not particularly limited, and styrene, isobutylene and the like are preferably used. The reaction conditions in the polymerization reaction of olefins are not particularly restricted, and the reaction conditions suitable for various raw materials can be adopted. However, when the reaction temperature exceeds 250° C., it is not preferred since the sulfonic acid group-containing carbonaceous material may decompose and a sulfonic acid group may be eliminated.

Also, the type of reactor to perform the polymerization reaction of olefins is not particularly limited, and any one of batch, continuous and semicontinuous types may be used. Also, any form of reactor such as tank reactor, column reactor and loop reactor may be used. The form of contacting the catalyst with the reactant may be any one of suspension phase, fixed bed and the like. In particular, the form that suspends the catalyst in a tank reactor equipped with a stirring apparatus or the form that continuously let flow the reactant through the catalyst in a fixed bed is preferably adapted.

The method for producing an alkylation reaction product of the present invention and method for producing an olefin polymer of the present invention are the methods using the solid acid catalyst of the present invention. Therefore, the process is simpler as compared to the conventional method using sulfuric acid, aluminum chloride, or boron trifluoride as a catalyst. In addition, in the method using sulfuric acid, aluminum chloride, or boron trifluoride as a catalyst, a neutralization and purification step is required for removal of the acid catalyst, and in the case of sulfuric acid catalyst, a concentration step and the like are required for reuse of the sulfuric acid, which complicate the process. However, in the method of the present invention, the catalyst can be easily separated by filtration, centrifugal separation or the like for reuse since the catalyst is solid, and the neutralization and purification step as in the method using sulfuric acid, aluminum chloride, or boron trifluoride as a catalyst is not required since the reaction product solution after removing the catalyst contains no acid catalyst component. After the catalyst removal, the product can be properly purified by distillation or the like. Reactive distillation can be also carried out.

Furthermore, if the solid acid catalyst of the present invention is used, the excellent heat resistance of the solid acid catalyst allows the reaction to be performed at high temperature. As a result, the reaction rate increased, so miniaturization of a reactor can be achieved. Also, the heat resistance of the catalyst decreased the frequency of catalyst exchange.

EXAMPLES

The present invention will be further specifically described based on Examples and Comparative Examples hereinbelow, but the present invention is not limited to the following Examples.

Example 1

Production of Sulfonic Acid-Containing Carbonaceous Material (Preparation of RF Wet Gel)

A 100-ml flask was charged with 11.1 g of resorcinol, 16.5 g of formaldehyde and 0.05 g of sodium carbonate, and 44 ml of distilled water was added thereto. The mixture was stirred, and after confirming that the ingredients were dissolved in water, the solution was allowed to stand at room temperature for 24 hours. Thereafter, the solution was heated at 70° C. for 8 hours, thereby gelating to give 71.0 g of RF wet gel.

(Preparation of RF Xerogel (Resorcinol Resin))

The amount 71.0 g of the resulting RF wet gel was dried in a vacuum at 70° C. for 8 hours, to give 14.7 g of resorcinol resin.

(Carbonization; Production of Carbon Xerogel)

The amount 5.4 g of the resulting resorcinol resin was put in a eggplant-shaped flask with a capacity of 200 ml and heat-treated at 500° C. for 4 hours under nitrogen flow to give 4.2 g of carbon xerogel.

(Sulfonation)

To 3.0 g of the carbon xerogel was added 150 g of concentrated sulfuric acid, and the mixture was heat-treated at 150° C. for 7.5 hours under nitrogen atmosphere, to perform sulfonation.

(Washing-Drying)

After the sulfonation, a black solid substance was filtered with a glass filter, and the residue was repeatedly washed with hot water under reflux (about 100° C.) using a Soxhlet extractor, to confirm that no sulfuric acid was detected in the washing water. The resulting substance was dried to give a black powder sulfonic acid group-containing carbonaceous material (hereinafter, referred to as "sulfonic acid group-containing carbonaceous material A").

Example 2

The same procedures as in Example 1 were carried out except that 25% fuming sulfuric acid is used instead of concentrated sulfuric acid as a sulfonating agent, to give a sulfonic acid group-containing carbonaceous material (hereinafter, referred to as "sulfonic acid group-containing carbonaceous material B").

Comparative Example 1

The procedures were carried out in the same conditions as in Example 1 using a novolac/hexamine resin as a raw material, to give a sulfonic acid group-containing carbonaceous material (hereinafter, referred to as "sulfonic acid group-containing carbonaceous material C"). The novolac/hexamine resin is a resin obtained by cross-linking and hardening a novolac type phenolic resin, obtained by polymerizing phenol and formaldehyde with an acid catalyst, with hexamethylenetetramine.

Comparative Example 2

The procedures were carried out in the same conditions as in Example 1 except that D-glucose was used as a raw material and the carbonization temperature was changed to 400° C., to give a sulfonic acid group-containing carbonaceous material (hereinafter, referred to as "sulfonic acid group-containing carbonaceous material D").

Example 3

Production of Sulfonic Acid-Containing Carbonaceous Material (Preparation of MRF Wet Gel)
A 100-ml flask was charged with 5.49 g of resorcinol, 4.71 g of phenol, 16.5 g of formaldehyde and 0.05 g of sodium carbonate, and 44 ml of distilled water was added thereto. The mixture was stirred, and after confirming that the ingredients were dissolved in water, the solution was allowed to stand at room temperature for 72 hours. Thereafter, the solution was heated at 80° C. for 8 hours, thereby gelating to give 68.0 g of MRF wet gel.
(Preparation of MRF Xerogel)
The amount 68.0 g of the resulting MRF wet gel was immersed in t-butanol at 50° C. for 2 hours, to replace with the solvent. Thereafter, this procedure was repeated twice. The resulting gel was dried in a vacuum at 60° C. for 8 hours, to give 12.8 g of MRF xerogel.
(Carbonization; Production of Carbon Xerogel)
The amount 9.3 g of the resulting MRF xerogel was put in a eggplant-shaped flask with a capacity of 200 ml, heat-treated at 250° C. for 7.5 hours and subsequently heat-treated at 500° C. for 2 hours under nitrogen flow, to give 6.9 g of carbon xerogel.

(Sulfonation)
To 3.1 g of the carbon xerogel was added 285 g of 15% fuming sulfuric acid, and the mixture was heat-treated at 150° C. for 2 hours under nitrogen atmosphere, to perform sulfonation.
(Washing-Drying)
After the sulfonation, a black solid substance was filtered with a glass filter, and the residue was repeatedly washed with hot water under reflux (about 100° C.) using a Soxhlet extractor, to confirm that no sulfuric acid was detected in the washing water. The resulting substance was dried to give a black powder sulfonic acid group-containing carbonaceous material (hereinafter, referred to as "sulfonic acid group-containing carbonaceous material E").
[Analyses of Carbon-Based Solid Acid]
The following analyses were carried out for each of the sulfonic acid group-containing carbonaceous materials obtained as described above.
<X-Ray Diffraction Analysis>
An X-ray diffractometer manufactured by MAC Science Co., Ltd (MXP18VAHF) was used for the analysis. As a result, no peak that could specify the structure was detected from the diffraction patterns of the sulfonic acid group-containing carbonaceous materials A, B and E of Examples 1 to 3, so the materials were found to be amorphous substances.
<Determination of Sulfonic Acid Group Content>
As described above, the sulfonic acid group content was determined by a method for determination of ion exchange capacity. The result is shown in Table 1.
<Elemental Analysis>
ElementarVario EL was used for the analysis. The result is shown in Table 1. In the case of the sulfonic acid group-containing carbonaceous materials A, B and E of Examples 1 to 3, sulfur was detected as S/C ratios of $1.6 \times 10^{-2}$, $2.6 \times 10^{-2}$ and $2.2 \times 10^{-2}$ respectively, to confirm that a sulfonic acid group was introduced.
<Degree of Graphitization>
Raman spectroscopy was performed to evaluate the degree of graphitization based on the peak intensity ratio of D-peak near 1400 $cm^{-1}$ and G-peak near 1580 $cm^{-4}$. A laser Raman spectroscopic analyzer HOLOLAB 5000R was used for the analysis. The result is shown in Table In the case of general carbonaceous materials, the peak intensity ratio of D-peak near 1400 $cm^{-1}$ and G-peak near 1580 $cm^{-1}$ in Raman spectroscopy is used as a measure of the degree of graphitization. However, the sulfonic acid group-containing carbonaceous materials A, B and E of Examples 1 to 3 did not give a clear G-peak and D-peak, so the peak intensity ratio could not be calculated.

TABLE 1

| | Production of Sulfonic Acid-Containing Carbonaceous Material | | | | | | | | Analysis Results of Sulfonic Acid-Containing Carbonaceous Material | | |
| --- | --- | --- | --- | --- | --- | --- | --- | --- | --- | --- | --- |
| | Type of Sulfonic Acid group-Containing | | Carbonization Conditions | | Sulfonation Conditions | | | Yield of Carbonized | Sulfonic Acid Group | Sulfur/ | Raman Spectroscopy |
| Ex. | Carbonaceous Material | Raw Material | Temperature (° C.) | Time (hour) | Sulfonating Agent | Temperature (° C.) | Time (hour) | material (%) | Content (mmol/g) | Carbon (mol/mol) × $10^{-2}$ | D/G Peak Intensity Ratio |
| Ex. 1 | A | Resorcinol resin | 500 | 4 | Concentrated sulfuric acid | 150 | 7.5 | 76 | 0.8 | 1.6 | No peak obtained |

TABLE 1-continued

| | Production of Sulfonic Acid-Containing Carbonaceous Material | | | | | | | Analysis Results of Sulfonic Acid-Containing Carbonaceous Material | | | |
|---|---|---|---|---|---|---|---|---|---|---|---|
| | Type of Sulfonic Acid group-Containing | | Carbonization Conditions | | Sulfonation Conditions | | | Yield of Carbonized | Sulfonic Acid Group Content | Sulfur/ Carbon | Raman Spectroscopy D/G Peak |
| Ex. | Carbonaceous Material | Raw Material | Temperature (°C.) | Time (hour) | Sulfonating Agent | Temperature (°C.) | Time (hour) | material (%) | (mmol/ g) | (mol/mol) × $10^{-2}$ | Intensity Ratio |
| Ex. 2 | B | Resorcinol resin | 500 | 4 | Fuming sulfuric acid | 150 | 7.5 | 76 | 1.2 | 2.6 | No peak obtained |
| Com. Ex. 1 | C | Novolac resin/ Hexamine | 500 | 4 | Concentrated sulfuric acid | 150 | 7.5 | 18 | 1.2 | 2.4 | No peak obtained |
| Com. Ex. 2 | D | D-Glucose | 400 | 4 | Concentrated sulfuric acid | 150 | 7.5 | 29 | 0.7 | 1.7 | 0.57 |
| Ex. 3 | E | MRF Xerogel | 500 | 2 | Fuming sulfuric acid | 150 | 7.5 | 74 | 1 | 2.2 | No peak obtained |

Alkylation Reaction

Reaction Example 1

Using the sulfonic acid group-containing carbonaceous material A as a solid acid catalyst, an alkylation reaction of toluene with benzyl chloride was carried out. The resulting product was benzyl toluene.

The reaction was performed as follows. The reaction pressure was all normal pressure.

A 200-cc glass container equipped with a stirrer was charged with 0.2 g of the powder sulfonic acid group-containing carbonaceous material A of the present invention, 0.3 mol of toluene and 0.03 mol of benzyl chloride. The temperature in the reaction container was raised to 100° C. while stirring, and the reaction was thereafter performed for 2 hours in that state. The reaction result is shown in Table 2.

Reaction Example 2

The same procedures were carried out as in Reaction Example 1 except that the sulfonic acid group-containing carbonaceous material B was used as a solid acid catalyst, to perform a benzylation reaction of toluene. The result is shown in Table 2.

Reaction Comparative Example 1

The same procedures were carried out as in Reaction Example 1 except that the sulfonic acid group-containing carbonaceous material C was used as a solid acid catalyst, to perform a benzylation reaction of toluene. The result is shown in Table 2.

Reaction Comparative Example 2

The same procedures were carried out as in Reaction Example 1 except that the sulfonic acid group-containing carbonaceous material D was used as a solid acid catalyst, to perform a benzylation reaction of toluene. The result is shown in Table 2.

TABLE 2

| Ex. | Type of Sulfonic Acid group-Containing Carbonaceous Material | Amount of Toluene in Starting Material (mol) | Amount of Benzyl Chloride in Starting Material (mol) | Reaction Temperature °C. | Benzyl Toluene Production Rate (μmol/ g-cat/hr) | Conversion of Benzyl Chloride % |
|---|---|---|---|---|---|---|
| Reaction Ex. 1 | A | 0.3 | 0.03 | 100 | 283 | 0.38 |
| Reaction Ex. 2 | B | 0.3 | 0.03 | 100 | 349 | 0.47 |
| Reaction Com. Ex. 1 | C | 0.3 | 0.03 | 100 | 56 | 0.07 |
| Reaction Com. Ex. 2 | D | 0.3 | 0.03 | 100 | 53 | 0.07 |

[Alkylation Reaction of Cumene with Styrene and Polymerization of Styrene]

Reaction Example 3

Using the sulfonic acid group-containing carbonaceous material A as a solid acid catalyst, an alkylation reaction of cumene with styrene was performed. The resulting product was 1-phenyl-1-isopropylphenyl ethane, styrene dimer and polymer. The reaction pressure was all normal pressure.

A 200-cc glass container equipped with a stirrer was charged with 0.2 g of the powder sulfonic acid group-containing carbonaceous material A of the present invention and 0.1 mol of cumene. Thereto was further added 0.01 mol of styrene, the temperature in the reaction container was thereafter raised to 140° C. While the stirring was continued with the temperature kept at 140° C., the reaction was performed for 1 hour. The reaction result is shown in Table 3.

Reaction Comparative Example 3

The procedures were carried out in the same conditions as in Reaction Example 3 except that the sulfonic acid group-containing carbonaceous material C was used as a solid acid catalyst, to perform a reaction. The result is shown in Table 3.

Reaction Comparative Example 4

The procedures were carried out in the same conditions as in Reaction Example 3 except that the sulfonic acid group-containing carbonaceous material 1) was used as a solid acid catalyst, to perform a reaction. The result is shown in Table 3.

Reaction Example 4

Alkylation Reaction of Cumene with Styrene and Polymerization Reaction Of Styrene The procedures were carried out in the same conditions as in Reaction Example 3 except that the sulfonic acid group-containing carbonaceous material E was used as a solid acid catalyst, to perform a reaction. The reaction result is shown in Table 3.

TABLE 3

| Ex. | Sulfonic Acid group-Containing Carbonaceous Material | Amount of Cumene in Starting Material (mol) | Amount of Styrene Monomer in Starting Material (mol) | Reaction Temperature °C. | Yield of Styrene Polymer (In terms of Styrene) (% by mole) | 1-Phenyl-1-Isopropylphenyl Ethane Production Rate (µmol/g-cat/hour) |
|---|---|---|---|---|---|---|
| Reaction Ex. 3 | A | 0.1 | 0.01 | 140 | 84 | 35 |
| Reaction Com. Ex. 3 | C | 0.1 | 0.01 | 140 | 3 | 1 |
| Reaction Com. Ex. 4 | D | 0.1 | 0.01 | 140 | 14 | 0 |
| Reaction Ex. 4 | E | 0.1 | 0.01 | 140 | 55 | 18 |

It can be seen from the Reaction Examples and Reaction Comparative Examples described above, that the sulfonic acid group-containing carbonaceous materials A, B and E of Examples 1 to 3 show more excellent reaction activities in nonpolar media like alkylation reaction and polymerization reaction of olefins, as compared to the conventionally known sulfonic acid group-containing carbonaceous materials C and D produced using novolac type phenolic resin, glucose or the like as a raw material.

INDUSTRIAL APPLICABILITY

The sulfonic acid group-containing carbonaceous material obtained by the production method of the present invention can be supplied in large amounts since the material can be easily and inexpensively produced, and the material has high activities as a solid acid catalyst in hydrophobic reaction media like alkylation reaction and polymerization reaction of olefins. Also, the sulfonic acid group-containing carbonaceous material is used as a catalyst, and thereby easily separated from the product, not requiring an aftertreatment such as neutralization and not requiring the steps of collecting and regenerating the catalyst, wastewater treatment and the like. Therefore, the productions of alkylation reaction product, olefin polymer and the like can be highly effectively performed.

The invention claimed is:
1. A method for producing a sulfonic acid group-containing carbonaceous material comprising a first step of carbonizing and sulfonating a polymer having a structural unit derived from resorcinol by heating in an inert gas atmosphere to obtain a sulfonic acid group-containing carbonaceous material, wherein
the first step comprises:
a second step of performing carbonization of the polymer in an inert gas atmosphere at a temperature of 300 to 600° C. for 1 to 100 hours and
a third step of performing sulfonation of a treated product obtained in the second step by concentrated sulfuric acid or fuming sulfuric acid having a mass 5 to 100 times the mass of the treated product.
2. The method for producing a sulfonic acid group-containing carbonaceous material according to claim 1, further comprising obtaining the polymer by addition condensation of resorcinol or a mixture comprising resorcinol and an aromatic hydroxy compound other than resorcinol with aldehydes in the presence of an acid catalyst or a basic catalyst.
3. The method for producing a sulfonic acid group-containing carbonaceous material according to claim 1, further comprising obtaining the polymer by addition condensation of resorcinol or a mixture comprising 50% by weight or more of resorcinol and 50% by weight or less of phenol with formaldehyde in the presence of a basic catalyst.
4. The method for producing a sulfonic acid group-containing carbonaceous material according to claim 2, wherein the basic catalyst is a sodium carbonate catalyst.
5. The method for producing a sulfonic acid group-containing carbonaceous material according to claim 1, further comprising obtaining the polymer by removing water and/or solvent from a gel comprising a reaction product by addition condensation reaction of resorcinol or a mixture comprising resorcinol and an aromatic hydroxy compound other than resorcinol with an aldehyde in the presence of a basic catalyst and the water and/or solvent.
6. The method for producing a sulfonic acid group-containing carbonaceous material according to claim 1, wherein the sulfonic acid group content of the sulfonic acid group-containing carbonaceous material obtained in the first step is 0.3 mmol/g or more.

7. A solid acid catalyst comprising a sulfonic acid group-containing carbonaceous material obtained by the production method according to claim 1.

8. A method for producing an alkylation reaction product comprising performing an alkylation reaction of the prescribed reaction substrate in the presence of the solid acid catalyst according to claim 7.

9. The method for producing an alkylation reaction product according to claim 8, wherein the reaction substrate is an aromatic compound.

10. The method for producing an alkylation reaction product according to claim 8, wherein the reaction substrate is a paraffinic hydrocarbon having a tertiary carbon atom.

11. A method for producing an olefin polymer comprising performing a polymerization reaction of olefins in the presence of the solid acid catalyst according to claim 7.

12. The method for producing a sulfonic acid group-containing carbonaceous material according to claim 3, wherein the basic catalyst is a sodium carbonate catalyst.

13. The method for producing a sulfonic acid group-containing carbonaceous material according to claim 5, wherein the basic catalyst is a sodium carbonate catalyst.

* * * * *